United States Patent [19]

Boylan et al.

[11] Patent Number: 4,877,616

[45] Date of Patent: Oct. 31, 1989

[54] PROCESS FOR PREPARING XEROSIN II AND XEROSIN III, IMPROVED BIOLOGICAL RESPONSE MODIFIERS

[76] Inventors: Elizabeth S. Boylan; Robert J. Boylan, both of 66 N. Chatsworth Ave., Larchmont, N.Y. 10538; Vincent Groupë, 7202 Lakeview Largo South - 143rd St. North, Largo, Fla. 34644; Robert W. Simpson, 261 Amwell Rd., R.D. #1, Neshanic Station, N.J. 08853

[21] Appl. No.: 179,471

[22] Filed: Apr. 8, 1988

[51] Int. Cl.$^4$ ............................................. A61K 35/74
[52] U.S. Cl. ................................... 424/123; 424/115; 435/170; 435/824
[58] Field of Search ..................... 424/115, 123, 195.1; 435/170, 824

[56] References Cited

U.S. PATENT DOCUMENTS 3,039,923  6/1962  Groupé et al. ........................ 424/115

OTHER PUBLICATIONS

"Effect of Chemotherapy on the dissemination of cancer and metastases", Franchi, G.; Donelli, M. and Rosso, R. CA 73(15): 75492c.

"Effect of some drugs on tumor dissemination and metastases", Rosso, R.; Donelli, M.; Franchi, G. and Garattini, S. CA 73(9): 43627j.

Primary Examiner—Jonnie R. Brown
Assistant Examiner—Jean C. Witz
Attorney, Agent, or Firm—Dominik, Stein, Saccocio, Reese, Colitz & van der Wall

[57] ABSTRACT

A water-soluble complex which is isolable from acid-precipitable material recovered from cultures of the bacterium, *Achromobacter xerosis*, and which is effective in inducing a variety of therapeutic responses commonly associated with biological responses modifiers and anti-inflammatory agents and which exhibits significant therapeutic activity in higher vertebrates at a dosage ranging from about 0.1 to about 25.0 mg/kg of body weight. Also disclosed are compositions containing such complexes, methods of preparation with such complexes and methods of treatment with compositions having such complexes.

2 Claims, 6 Drawing Sheets

BIOLOGICAL RESPONSES MODIFIED BY *XEROSIN*[a]

| HOST | RESPONSE | INITIATED BY |
|---|---|---|
| MOUSE | PNEUMONIA | INFLUENZA A VIRUS<br>INFLUENZA B VIRUS<br>NEWCASTLE VIRUS<br>ENDOTOXIN LIPOPOLYSACCHARIDE B<br>FRB POLYSACCHARIDE<br>*MIYAGAWANELLA FELIS* |
| MOUSE | CONVULSION AND DEATH<br>PARALYSIS AND DEATH | INFLUENZA A VIRUS<br>NEWCASTLE VIRUS |
| RAT | FOOT PAD EDEMA | CARRAGEENIN |
| GUINEA PIG | ABSCESS<br>ERYTHEMA AND INDURATION<br>TUBERCULIN REACTION<br>PASSIVE ARTHUS REACTION | TURPENTINE<br>UREASE<br>TUBERCULIN<br>BOVINE SERUM ALBUMIN |
| CHICKEN | TUMOR GROWTH | ROUS SARCOMA VIRUS |

[a] ACID PRECIPITABLE MATERIAL DERIVED FROM *ACHROMOBACTER XEROSIS.*

FIG. 2A

PREPARATION OF XEROSIN II

HOMOGENIZE 1-2% CRUDE XEROSIN IN DISTILLED WATER
ADJUST TO PH 9, HEAT FOR 15 MIN AT 80°C
REDUCE PH TO 7, CENTRIFUGE AT 12,000 X G

→ SUPERNANTANT

PELLET
DISCARD

ADD SODIUM SULFATE TO 0.02M AND
CETYLTRIMETYLAMMONIUM BROMIDE
WARM AT 37°C FOR 1 HR, CENTRIFUGE

→ SUPERNTANT

PELLET
DISCARD

COLLECT ACETONE PRECIPITATE
AFTER 18-24 HRS AT 4 OR -20°C

DISOLVE PRECIPITATE IN WATER
ADJUSTED TO PH 9

REDUCE PH TO 7.5 AND LYOPHILIZE

= XEROSIN II

FIG. 2B

EFFECT OF XEROSIN II ON CHEMICAL (LPS) AND VIRAL (NDV) PNEUMONIA IN MICE

| GROUP NO | INTRANASAL CHALLENGE AGENT | DOSE OF XEROSIN II (MG/KG) | AVERAGE LUNG WEIGHT (MG) | CHANGE OF MEAN LUNG WEIGHT (MG) | LUNG LESION SCORE (%LIM) |
|---|---|---|---|---|---|
| 1 | LPS | 12.5 | 215 | $-149^b$ | 30 |
| 2 | | 6.25 | 238 | $-126^b$ | 20 |
| 3 | | 2.5 | 293 | $-71^b$ | 38 |
| 4 | | 0 | 364 | $+180^c$ | 81 |
| 5 | NDV | 12.5 | 205 | $-117^b$ | 48 |
| 6 | | 6.25 | 250 | $-72^b$ | 48 |
| 7 | | 2.5 | 243 | $-79^b$ | 58 |
| 8 | | 0 | 322 | $+138^c$ | 85 |
| 9 | PBS | 0 | 184 | — | 0 |

DELAYED APPEARANCE OF PALPLE MAMMARY TUMORS INDUCED BY DMBA IN RATS TREATED WITH XEROSIN II

| TREATMENT[a] | GROUP SIZE | TIME (WKS) WHEN 50% OF DMBA TREATED RATS HAD DEVELOPED AT LEAST ONE PALPABLE MAMMARY TUMOR[b] |
|---|---|---|
| EXPERIMENT 1 | | |
| XEROSIN – WEEKS 2-5 POST DMBA | 24 | 21.5 (20.6 – 22.7)[c] |
| SALINE – WEEKS 2-5 POST DMBA | 25 | 17.8 (17.3 – 18.4) |
| EXPERIMENT 2 | | |
| XEROSIN – WEEKS 5-8 POST DMBA | 30 | 23.9 (22.3 – 26.7)[d] |
| SALINE – WEEKS 5-8 POST DMBA | 30 | 22.0 (20.5 – 24.5) |

FIG. 7

EFFECTS OF XEROSIN II ON SURVIVAL OF RATS BEARING 13762 MAMMARY ADENOCARCINOMA

| TREATMENT | $ST_{50}$[a] | SURVIVORS AT TERMINATION[b] | INCIDENCE OF METASTASES AT DEATH OR KILLING(%) | | |
|---|---|---|---|---|---|
| | | | LUNGS | LYMPH NODE[c] | VISCERAL[d] |
| TRIAL 1 | | | | | |
| TUMOR + XEROSIN | 40.9[e] (39.9–42.5) | 12/27 (44%) | 96 | 50 | 50 |
| TUMOR + SALINE | 36.8 (35.8–38.1) | 5/20 (25%) | 90 | 40 | 55 |
| TRIAL 2 | | | | | |
| TUMOR + XEROSIN | 47.0[e] (44.9–51.8) | 8/16 (50%) | 80 | 53 | 27 |
| TUMOR + SALINE | 38.6 (37.4–39.8) | 4/17 (24%) | 93 | 87 | 13 |

PURIFICATION OF XEROSIN:

PROCESS FOR PREPARING XEROSIN II AND XEROSIN III, IMPROVED BIOLOGICAL RESPONSE MODIFIERS

BACKGROUND OF THE INVENTION

This invention relates to biological response modifiers and anti-inflammatory agents and, more particularly, to Xerosin complexes, compositions containing such complexes, methods of preparing such complexes and methods of treatment with compositions having such complexes.

DESCRIPTION OF THE BACKGROUND ART

In medicine, a wide variety of anti-inflammatory agents have been known and utilized for years. By way of example, cortico-steroids, e.g., cortisone, have been used to treat arthritis and a wide variety of other diseases. Such treatments are effective for reducing inflammation associated with many diseases. Unfortunately, however, such treatment often produces serious side effects such as disturbances in salt blood balance in blood and decreased resistance to infection.

Recent scientific advances have resulted in a new class of drugs known as "biological response modifiers" which also have anti-inflammatory properties but do not have the negative side effects such as those attendant with cortico-steroids.

By way of example, an early biological response modifier was described in U.S. Pat. No. 3,039,923 issued to Groupé et al. Such patent, however, described the technical advance as an unusual anti-inflammatory agent because this new class of drugs had not yet been created. Such technical advance was known as Xerosin APM, an acid precipitable material. Such material was a relatively unrefined or crude precurser of the invention described herein. Its manufacture included the step of culturing *Achromobacter Xerosin* No. 134, a strain of which was deposited in the culture collection of the Institute of Microbiology of Rutgers, the State University, New Brunswick, New Jersey. Such culture collection has been transferred to American Type Culture Collection at Rockville, Maryland.

In a subsequent patent, U.S. Pat. No. 3,531,567 to Berger et al, essentially the same crude material was disclosed as the material of the Groupé el al patent. Its identity as a biological response modifier was still unappreciated. Its method of preparation, however, was different.

As illustrated by a large body of prior art including the above-noted patents and a large number of publications, efforts are continuously being made in an attempt to improve biological response modifiers. Nothing in the prior art, however, suggests the present inventive combination of materials and method steps as herein described and claimed. The present invention achieves its purposes, objects and advantages over the prior art through new, useful and unobvious materials and method steps which increase effectiveness.

Therefore, it is an object of this invention to provide water-soluble complexes which are isolatable from acid precipitable material recovered from cultures of the bacterium, *Achromobacter xerosis*, and which are effective in inducing a variety of therapeutic responses and which exhibit significant therapeutic activity in higher vertebrates at a dosage ranging from about 0.1 to about 25.0 mg/kg of body weight and to provide compositions containing such complexes, methods of preparing such complexes and methods of treatment with compositions having such complexes.

It is still a further object of this invention to prepare new and improved biological response modifiers.

These purposes, objects and advantages should be construed as merely illustrative of some of the more prominent features and applications of the present invention. Many other beneficial results can be attained by applying the disclosed invention in a different manner or by modifying the invention within the scope of the disclosure. Accordingly, other purposes, objects and advantages as well as a fuller understanding of the invention may be had by referring to the summary of the invention and detailed description describing the preferred embodiment of the invention in addition to the scope of the invention as defined by the claims taken in conjunction with the accompanying drawings.

SUMMARY OF THE INVENTION

The present invention is defined by the appended claims with features of the specific embodiments illustrated in the attached Figures. For the purpose of summarizing the invention, the invention may be incorporated into a water-soluble complex which is isolable from acid precipitable material recovered from cultures of the bacterium *Achromobacter xerosis* and which is effective in inducing a variety of therapeutic responses and which exhibits significant therapeutic activity in higher vertebrates at a dosage ranging from about 0.1 to about 25.0 mg/kg of body weight. The complex has a molecular weight under approximately 100,000. The acid precipitable material is purified by absorption chromatography of other methodologies.

The invention may also be incorporated into a composition useful in a variety of therapeutic responses in higher vertebrates comprising, as an active ingredient, an effective amount of the complex as defined above, in the form of a neutral aqueous solution or other forms.

The invention may also be incorporated into a method of preparing the complex as defined above comprising: growing a suitable culture of the bacterium, *Achromobacter xerosis*, in a suitable growth medium using minimal agitation to achieve a relatively low oxygen tension; recovering a water solubilized substance from acid precipitable material isolated from the used culture medium in a conventional manner; lyophilizing the water solubilized precipitable to dryness from a frozen state; homogenizing the lyophilized product in distilled water at about pH 9; heating the resultant solution readjusted to about pH 9 at about 80 degrees C. for about fifteen (15) minutes; adjusting the solution to about pH 7; removing insoluble material by centrifugation; adding sodium sulfate to a final concentration of about 0.02M; adding cetyltrimethylammonium bromide stock solution to about a 0.3% final concentration; warming the resultant solution at about 37 degrees C. for about one (1) hour to form a precipitate; clarifying the solution by centrifugation; adding cold acetone to form a further precipitate; collecting the precipitate by centrifugation; and washing the precipitate with acetones. The acetone precipitated material was washed twice with acetone, dissolved in water at pH 9 by mechanical homogenization, and adjusted to about pH 7.5 prior to lyophilization. The final product, Xerosin II, was solubilized in PBS or saline. For Xerosin III, the method includes the further step of purifying the precipitation by hydroxyapatite chromatography in a calcium phosphate column. An additional recovery of acid precipitable material includes a physical disruption of cells of the bacterium *Achromobacter xerosis* after removal of bacterial cellular material prior to the utilization of the used medium as described above. The method as defined above, further comprises dissolving the purified Xerosin II precipitate by homogenation in water adjusted to about pH 9; adjusting the resultant solution to about pH 7.5; and then lyophilizing to dryness from a frozen state results in composition which retains biological activity for long periods of time when stored in a closed container at room temperature.

The invention may also be incorporated into the method for inducing therapeutic responses in higher vertebrates comprising administering to a human or animal patient a therapeutically effective amount of a composition comprising a complex as defined above as an active agent. The composition is administered in an amount sufficient to induce a therapeutic response in the patient. The therapeutic response is directed to treatment of diseases commonly affected by biological response modifiers and anti-inflammatory agents.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiment may be readily utilized as a basis for modifying or designing other materials and methods for carrying out the same purposes and objectives of the present invention. It should be realized by those skilled in the art that such equivalent materials and methods do not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which.

DETAILED DESCRIPTION OF THE INVENTION

Xerosin (APM) is described in U.S. Pat. No. 3,039,923 issued to Groupé et al.

Figure 1:
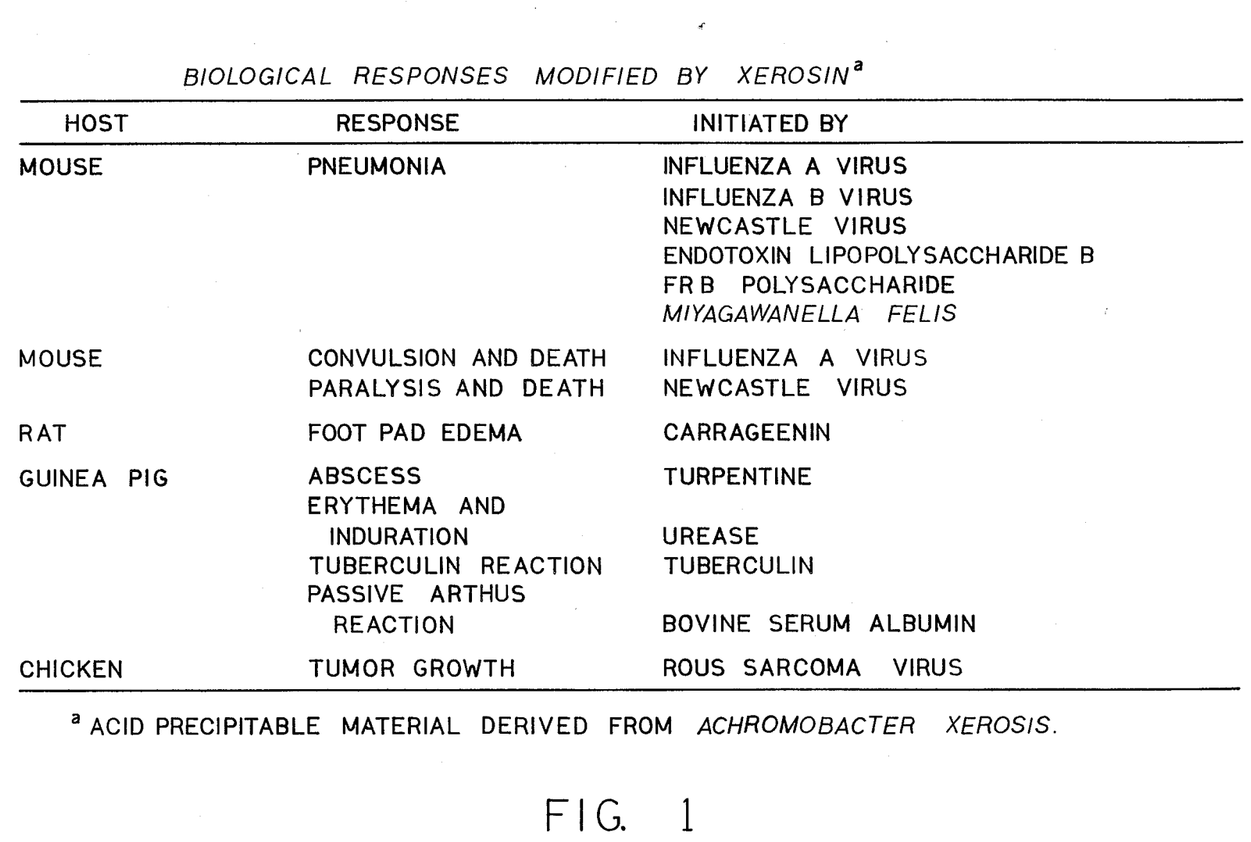
FIG. 1 is a table illustrating certain biological responses modified by Xerosin APM.

The ability of an acid precipitable material (APM) of the bacterium *Achromobacter xerosis (A. xerosis)* to suppress viral pneumonia in mice was first described by Groupé et al in their aforementioned patent. Subsequently, the broader efficacy of such bacterial product, termed Xerosin or Xerosin APM was demonstrated in a variety of est animal test systems. Note FIG. 1.

The present disclosure relates to Xerosin II and Xerosin III and their new biological activities. Xerosin II and Xerosin III are refined products from the bacterium *Achromobacter xerosis* known as Xerosin or Xerosin (APM). The initial culture described in the aforementioned Groupé et al patent is the same as the initial culture utilized in the present invention, and the subject matter of the aforementioned Groupé patent application is incorporated herein by reference.

Figure 2A:
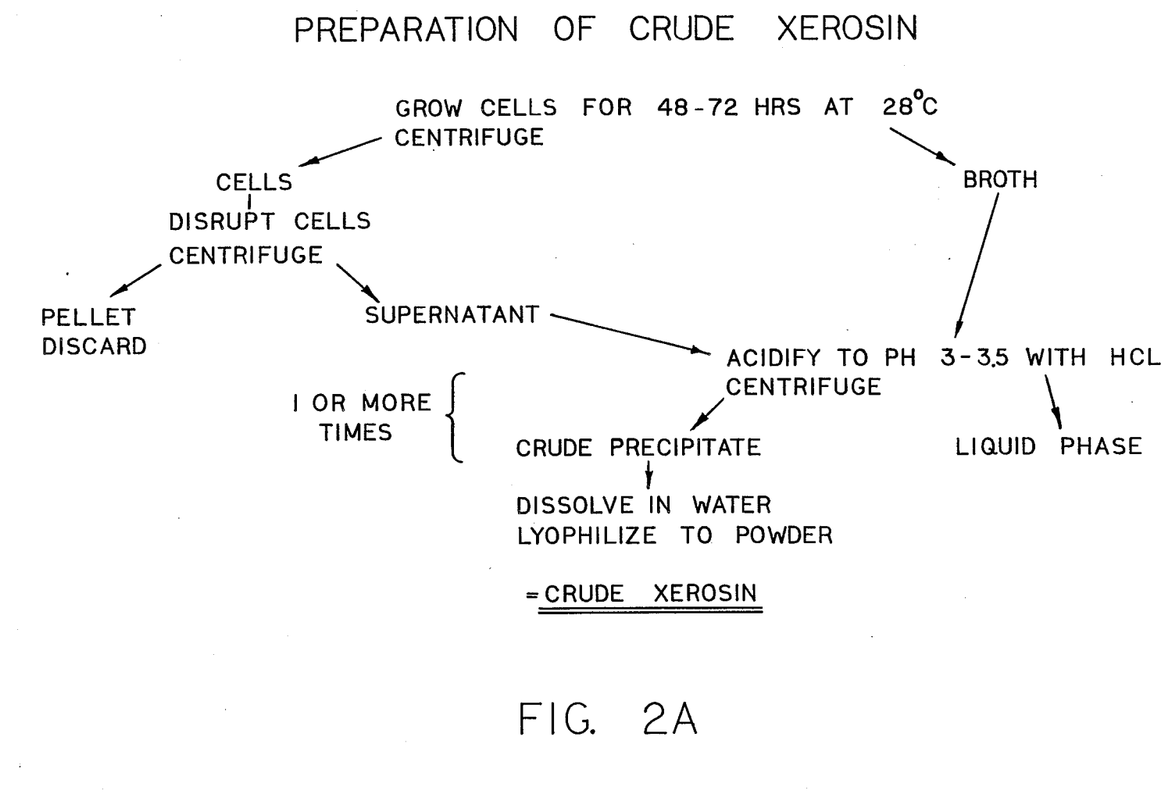
FIGS. 2A and 2B are flow diagrams of the methods of preparing crude Xerosin, simply called Xerosin or Xerosin (APM) and Xerosin II.
Figure 2B:
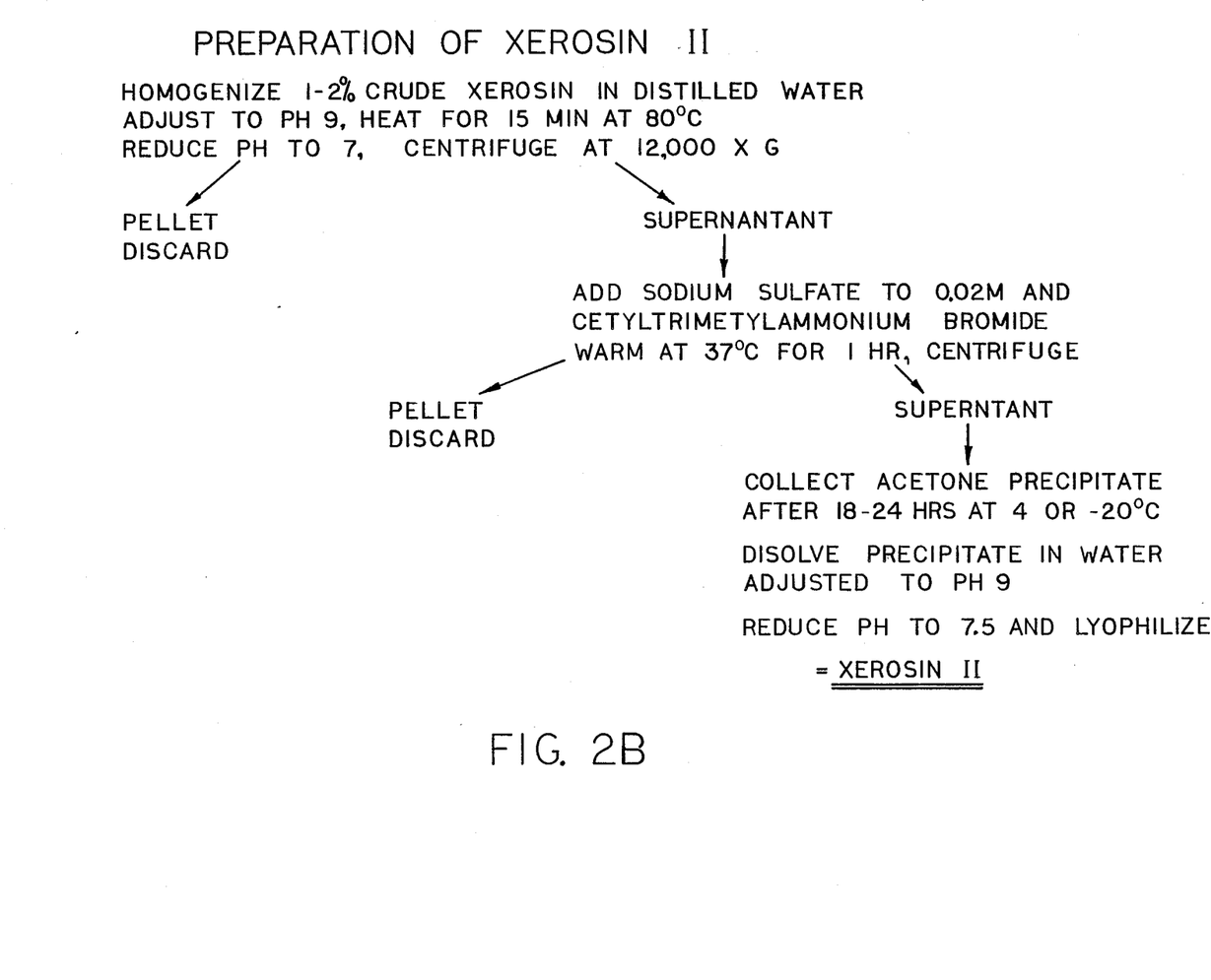

FIGS. 2A and 2B schematically illustrate the steps employed in the preparation of Xerosin (APM) and Xerosin II. Broadly speaking, the method comprises the steps of first growing a suitable culture of the bacterium *Achromobacter xerosis* in a suitable growth medium using minimal agitation to achieve a relatively low oxygen tension. Thereafter, a water solubilized precipitate is recovered from acid precipitable material (APM) isolated from the culture in the conventional manner. Note the aforementioned Groupé patent. The conventional recovery of acid precipitable material includes a physical disruption of cells of the bacterium *Achromobacter xerosis* prior to removal of bacterial cellular material. To prepare Xerosin II from Xerosin (APM), the first step is lyophilizing of the water solubilized precipitate to dryness from a frozen state. The lyophilized product is than homogenized in distilled water at about pH 9. Thereafter, the resultant solution is readjusted to about pH 9 and heated at about 80 degrees C. for about fifteen (15) minutes. The next steps are the adjusting of the solution to about pH 7 and the removing of insoluble material by centrifugation. Sodium sulfate is then added to a final concentration of about 0.02M (Molarity). Cetyltrimethylammonium bromide stock solution is then added to about a 0.3% final concentration. The resultant solution is then warmed at about 37 degrees C. for about one (1) hour to from a precipitate. The solution is then clarified by centrifugation. To prepare Xerosin III from Xerosin II, cold acetone is then added to form a further acetone precipitate. The acetone precipitated material was washed twice with acetone, dissolved in water at pH 9 by mechanical homogenization, and adjusted to about pH 7.5 prior to lyophilization. The final product, Xerosin II, was solubilized in PBS or saline. The further precipitate is next collected by centrifugation, washed with acetone and purified by hydroxyapobite chromatography in a calcium phosphate column. The method further comprises, as the final steps for Xerosin II preparation, the steps of dissolving the purified acetone precipitate by homogenation in water adjusted to about pH 9 followed by adjusting the resultant solution to about pH 7.5, and then lyophilizing to dryness from a frozen state results in a composition which retains biological activity for long periods of time when stored in a closed container at room temperature.

In the preparation of Xerosin III, material prepared as described above, Xerosin II, is suspended in glass-distilled water up to a concentration of 10 mg of material per ml. The pH is adjusted to 9.0 with NaOH and the suspension is heated at 80 degrees C. for twenty (20) minutes. The suspension is cooled to 4 degrees C. and centrifuged at 4 degrees C. at twelve-thousand (12,000) times gravity for ten (10) minutes to remove particulate matter. The supernatant is adjusted to pH 6.8 with HCl and passed through successive Millipore filters, the final one having a pore size of 0.45 μm. The suspension is stored in a sterile container.

The suspension is subjected to adsorption chromatography using a hydroxyapatite-agarose gel medium identified as HA-Ultrogel and manufactured by LKB-Produckter, Sweden. The directions of the manufacturer found in the instruction Manual for HA-Ultrogel are followed. The suspension is brought to 5 μM potassium phosphate (K-PO), pH 6.8 and applied to the column. Elution is stepwise within 5 μM, 100 μM, 300 μM and 500 μM K-PO, pH 6.8 and the elutant monitored at a wavelength of 280 nm. Elution with the various ionic strength buffers is continued until the absorbency approaches the baseline and then the next higher ionic-strength buffer is used for Elution.

Xerosin III, the fraction eluted from hydroxyapatite columns with 0.1 molar potassium phosphate, has the following properties:
A. Water soluble
B. Low molecular weight, 10,000 to 100,000
C. High biological activities, comparable to penicillin in dosage for its therapeutic response in animals
D. Low endotoxic level
E. Recovery—about 6%

Xerosin III constitutes a major step further in the purification of Xerosin. Xerosin III was obtained from Xerosin II, which was obtained from Xerosin APM. Xerosin III is of particular importance because of its low toxicity, markedly increased (100 times) potency and lower molecular weight. Other fractions derived from hydroxyapatite chromatography were also very active in the mouse pneumonia assay. These were eluted with 5 μM and 300 μM phosphate buffer, pH 6.8.

More specifically, with regard to the method of preparation, the bacterium, *Achromobacter xerosis*, was grown for fourty-eight (48) hours at 28 degrees C. in a 1,000-L capacity fermentation tank under conditions of limited aeration by mechanical stirring using sterile broth medium of the following typical composition; 0.5% $K_2HPO_4$, 0.3% $KH_3$ $PO_4$, 0.5% yeast extract, 0.01% $MgSO_4 \cdot 7$ $H_20$ and 1% dextrose, separately sterilized, in tap water. After fermentation, the cells were removed in a continuous-flow centrifuge and the supernatant fluid was acidified to ph 3.0–3.5 by addition of concentrated HCl. The visible flocculent precipitate, crude Xerosin, homogenized in PBS at ph 9 was heated at 80 degrees C. for fifteen (15) minutes, clarified by centrifugation, and adjusted to ph 7.

Final concentrations of 0.02M sodium sulfate and 0.3% cetyltrimethylammonium bromide (CTAB) were added followed by incubation at 37 degrees C. for sixty (60) minutes. The solution was centrifuged to remove the CTAB precipitated material, which was discarded. Two volumes of cold acetone were added to the supernatant fluid and precipitation was carried out overnight at −20 degrees C.

Visual inspection of the solution before and after Millipore filtration clearly showed that such filtration removed a substantial but unknown amount of material from the solution injected. The dosages of Xerosin II are considerably lower in mg/kg than those reported herein for all experiments involving rat tumors.

Injections of DMBA-treated rats with Xerosin II or saline began two (2) weeks after administration of the carcinogen and proceeded three (3) times a week for four (4) weeks. Each injection contained 2.4 mg Xerosin II in 0.5 ml for a dose of 12 mg/kg body weight. Rats weighed approximately 200 g at the start of treatment. Rats bearing the 13762 mammary tumor received 12 injections of Xerosin II three (3) times per week beginning three (3) days following tumor implantation. Each 0.5 ml injection produced a dose of 30 mg/kg body weight. The rats weighed approximately 75 g at the start of the experiment. All injections were delivered subcutaneously in the midventrolateral region.

The action of Xerosin II reduced both lung lesion scores and mortality in mice treated intranasally with Newcastle disease virus (NDV) or with endotoxin, lipopolysaccharide B (LPS). Xerosin II was also used to treat rats with two rat tumor systems. Mammary tumors induced in rats by 7, 12-dimethylbenz(a)anthracene (DMBA) have been used extensively as a model system o study the initiation, hormonal dependence, and chemotherapy of breast cancer. However, unlike human breast cancer, primary mammary tumors induced by DMBA rarely invade surrounding tissues or metastasize to distant sites. Effects of modifying agents in this system are usually measured in terms of changes in incidence of tumor-bearing animals, in tumor multiplicity, or in tumor latency. The 13762 mammary tumor line was derived from a DMBA-induced tumor in the Fischer 344 rat, but does invade local tissues and spreads through the lymphatics and bloodstream to regional lymph nodes and distant organs, most commonly the lungs. Therapeutic effects can be measured in terms of control of tumor growth or metastatic spread or as increased survival. This tumor line has been used previously to study the effects of surgery chemotherapy, and immunotherapy. Thus, the DMBA-induced primary tumors and the 3762 transplantable tumor line complement one another as model systems providing the opportunity to test the effects of compounds like Xerosin on various aspects of cancer development and growth.

For the experiments, Swiss-Webster mice were obtained from Perfection Breeders of Douglassville, Pennsylvania while all rats were obtained from the Charles River Breeding Laboratories, Wilmington, Maryland and maintained in a temperature-controlled facility on a 12 hour/12 hour, light/dark cycle. Purina Rat Chow from Ralston-Purina Company, St. Louis, Missouri and tap water were provided ad libitum; bedding material consisted of hardwood shavings. For experiments using DMBA, seven (7) week old female rats of the noninbred CD strain, Sprague-Dawley derived, were used. Experiments with the 13762 tumor utilized the syngeneic Fischer 344 rat; implantations were made in five (5) to six (6) week old females.

The mouse pneumonia protection test, originally described by Groupé and co-workers was used to assess the biological activity of Xerosin II preparations. Groups of ten (10) or twenty (20) Swiss-Webster mice 18–20 g each were lightly anesthetized with ether and immediately administered 75-l volumes of either Difco *Escherichia coli* LPS or egg-grown NDV, California strain of Newcastle disease virus, by intranasal instillation. These challenge agents were diluted in phosphate-buffered saline (PBS), and the doses used produced 20-30% mortality and sever pneumonia in surviving animals of the positive control group. Approximately three (3) hours after challenge, appropriate groups of animals received subcutaneous injections with 0.5-ml volumes of Xerosin diluted in PBS. Single subcutaneous injections followed on days one (1) and two (2) after challenge. On the third day after intranasal instillation, the lungs of all mice were scored for lesions and lung weights were determined. A lung weight reduction of greater than 75 mg and a greater than or equal to 50% reduction of lung lesion score, by comparison with the positive control mice, were considered evidence for strong therapeutic activity in these teats.

Solutions of DMBA, Eastman Organic Chemicals, Rochester, New York were made up in sesame oil the afternoon before use. During stirring at room temperature, the DMBA solution was kept in a foil-wrapped container to prevent photodegradation. Each rat, fourty-eight (48) to fifty (50) days of age, received a single gastric intubation of 15 mg DMBA in 1 ml sesame oil. Control animals received intubations of vehicle alone. Beginning five (5) to six (6) weeks after DMBA intubation, rats were palpated twice a week for the presence of mammary tumors. Tumor size was assessed by means of caliper measurement of two (2) diameters and expressed as the geometric means of tumor diameters.

Rats bearing the 13672 transplantable mammary adenocarcinoma were provided originally by the Breast Cancer Task Force (BCTF) Tumor Bank maintained by the Mason Research Institute, Worcester, Massachusetts. The tumor line has been maintained by routine transplantation in this laboratory since 1981. Transplant procedures followed recommendations from the BCTF Tumor Bank. Briefly, rats bearing fifteen (15) to nineteen (19) day old tumors were killed by asphyxiation with $CO_2$. The tumor was removed aseptically and rinsed in ice-cold Hanks' balanced salt solution, Difco Laboratories, Detroit, Michigan. Trimmed pieces of healthy tumor were cut into 1-$mm^3$ fragments and inserted subcutaneously using stainless-steel trocars, 13 gauge. Care was taken to implant all tumors in comparable subcutaneous locations in the ventrolateral region between gland areas three (3) and four (4). All implantations were performed within thirty (30) minutes of the time of death. Tumor growth was measured with calipers.

Data on tumor incidence were analyzed by the probit method of Finney using the PROBIT procedure of the Statistical Analysis System, SAS Institute, Box 8000, Cary, N.C.

Figure 3:
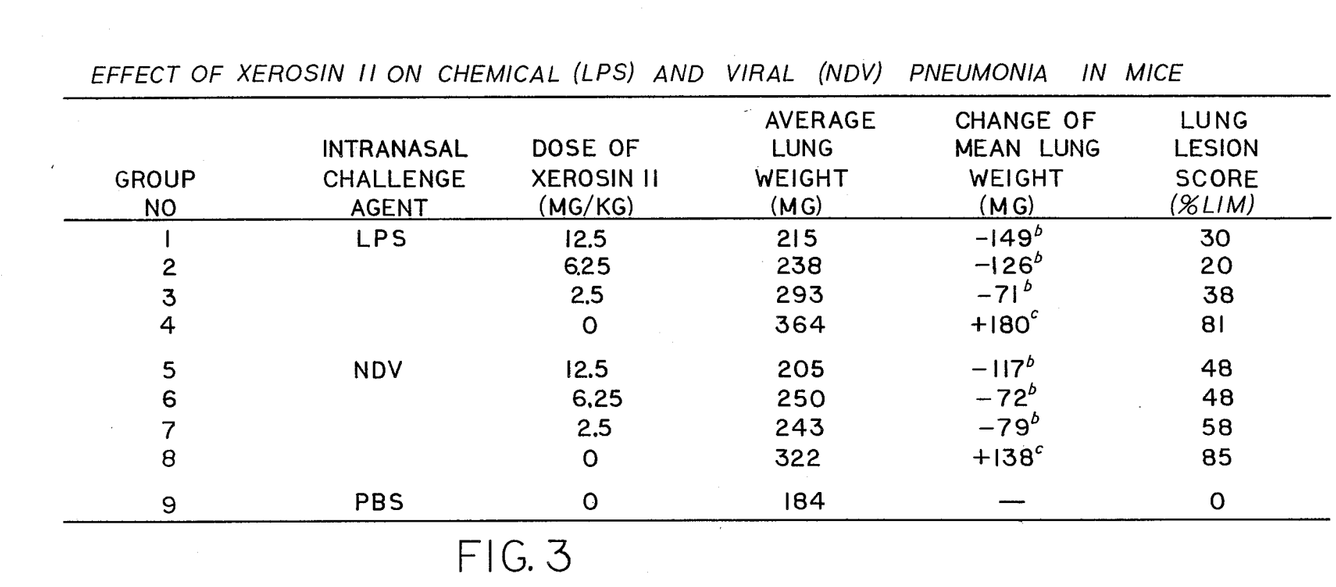
FIG. 3 is a table illustrating the effect of Xerosin II on chemical (LPS) and viral (NDV) pneumonia in mice.

Results of a representative test using Xerosin II to reduce the severity of pneumonia induced in mice by NDV or endotoxin are presented in FIG. 3.

In the table of FIG. 3, the mice received 75-$\mu$g volumes of either 50 $\mu$g lipopolysaccharide B (LPS), egg-grown Newcastle disease virus (NDV), or phosphate-buffered saline (PBS) by the intranasal route. Beginning three (3) hours after challenge and on days one (1) and two (2) thereafter, the mice received single subcutaneous injections of either Xerosin II or PBS. Lung lesion scores and lung weights were determined on day three (3). The lung lesion score (%L/M) equals the total lesion score divided by total maximum lesion score multiplied by 100. Scoring was: 1=10-24%; 2=25-49%; 3=50-74%; 4=75-100% consolidated tissue; 5=dead mouse with 75-100% consolidation. A maximum score of 100 represents a group with all mice dead at day three (3) with lungs showing 75-100% consolidation. In the "change of mean line weight (mg)" column of FIG. 3, for groups 1, 2, 3, 6, 7 and 8, the change in wet weight of lungs of Xerosin II-treated mice compared with LPS- or NDV-treated groups receiving PBS treatment only (groups one (1) to three (3) vs. four (4) or groups five (5) to seven (7) vs. eight (8) while for groups four (4) and eight (8) the change in wet weight of lungs of LPS- or NDV-treated mice compared with group receiving single intranasal treatment with 75 $\mu$g of PBS (groups 1-8 vs. 9).

Figure 4:
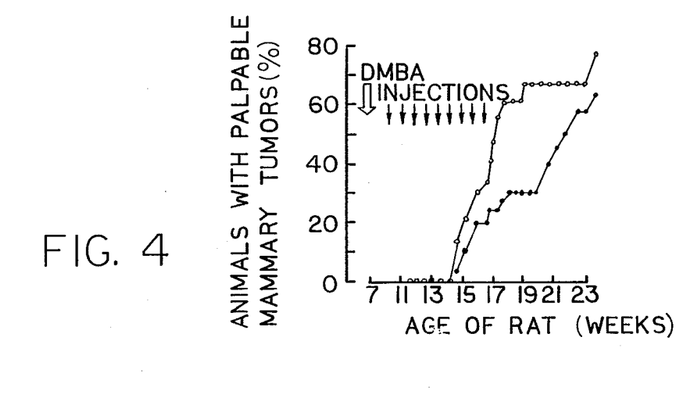
FIG. 4 is a graph of the percent of animals with palpable mammary tumors plotted against the age of the rats in weeks.

FIG. 4 shows the effect of Xerosin II administered early during the initiation phase of two (2) to five (5) weeks after DMBA treatment on the incidence of tumor-bearing rats.

FIG. 4 illustrates the incidence of tumor-bearing animals following intubation of 15 mg of 7, 12-dimethylbenz(a)anthracene (DMBA) at seven (7) weeks of age indicated by the large arrow. Xerosin-treated animals, twenty-four (24) in number, are plotted as filled circles and received twelve (12) injections of Xerosin (2.4 mg each, 12 mg/kg body weight) three (3) times per week beginning at nine (9) weeks of age indicated by the small arrows. Saline-treated control animals, twenty-five (25) in number received injections of saline and are plotted as open circles. Animals were palpated biweekly beginning 4.5 weeks after DMBA intubation.

Although tumors began appearing at approximately the same time in both the Xerosin and saline-treated groups, there was an effective suppression in the number of rats with tumors up to twenty (20) weeks of age, thirteen (13) weeks post DMBA, associated with Xerosin II treatment. When these data were analyzed, the Xerosin-treated group demonstrated a statistically significant delay in tumor development compared with controls. Note FIG. 5.

Figures 5, 6:
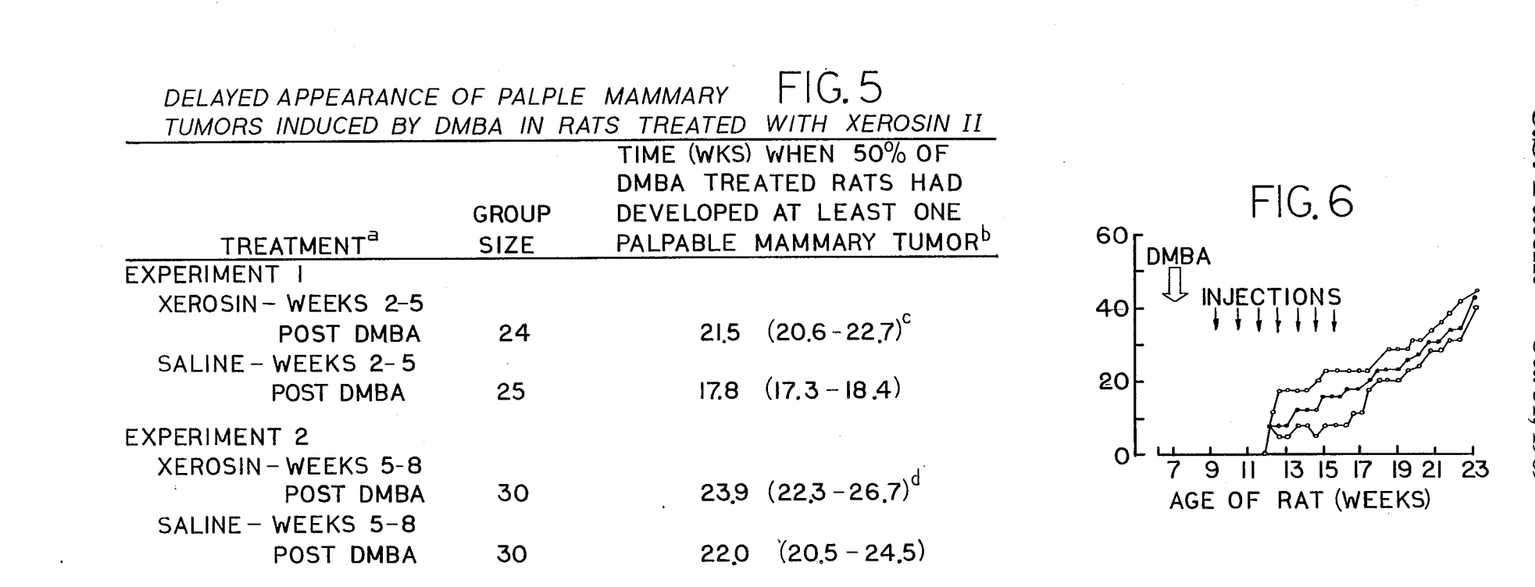
FIG. 5 is a table illustrating the delayed appearance of palpable mammary tumors induced by DMBA in rats treated with Xerosin II.
FIG. 6 is another graph of the percent of animals with palpable mammary tumors plotted against the age of the rats in weeks.

In the table of FIG. 5, all rats were fourty-eight (48) to fifty (50) days of age when treated with 15 mg i.g. 7, 12-dimethylbenz(a)anthracene (DMBA). Treatment with Xerosin II or saline began two (2) or five (5) weeks after DMBA intubation and continued three (3) times per week for four (4) weeks. Each subcutaneous injection (0.5 ml) contained 2.4 mg Xerosin II for a dose of 12 mg/kg starting body weight. Development of tumors was determined from biweekly palpations by probit method of Finney. The numbers in parentheses in the last column represent fiducial limits. The time in weeks of the Xerosin II rats in the first group was significantly different from control (p less than or equal to 0.05) while the Xerosin II rats of the second group was not significantly different from control.

Approximately two (2) months following the final Xerosin II injection, animals in the Xerosin-treated group began to develop tumors at an increased rate, with the incidence of tumor-bearing rats becoming comparable with that of the saline-treated group by twenty-three (23) weeks of age. No effect could be demonstrated on tumor multiplicity, i.e., number of tumors per tumor-bearing rats.

To determine whether Xerosin II treatment could affect the carcinogenic process at a later point, DMBA-treatment animals were injected with Xerosin II over a four (4) week period beginning five (5) weeks after carcinogen treatment, just after the first tumors become palpable. Note FIG. 6.

FIG. 6 shows the incidence of tumor-bearing animals following intubation of 15 mg 7, 12-dimethylbenz(a)anthracene (DMBA) at seven (7) weeks of age, note the large arrow. Xerosin-treated animals, thirty (30) in number and shown as filled circles, received twelve (12) injections of Xerosin (2.4 mg each, 12 mg/kg body weight) three (3) times per week beginning at twelve (12) weeks of age, note the small arrows. Saline-treated control animals, thirty (30) in number and shown as open circles, received injections of saline as indicated above. The regression of palpable tumors in Xerosin-treated animals is also plotted. Note the circles with lines. Atypical small masses in two animals that ulcerated through the skin and healed were not included in the data on the saline-treated controls.

While the Xerosin-treated group had a lower incidence of tumor-bearing animals during the Xerosin II treatment period, the difference was not as dramatic as in the previous experiment, and the delay in appearance of tumors in the Xerosin-treated group did not reach statistical significance. Note again FIG. 5. Again, the effect of the Xerosin II treatment was overcome in time after Xerosin II therapy was discontinued. When the complete regression of two tumors in two animals from the Xerosin-treated group was considered in calculation of the data, the difference between the Xerosin and saline-treated groups was increased. Tumor multiplicity was not affected by this Xerosin II treatment protocol, consistent with the results of the previous experiment.

Figure 7:
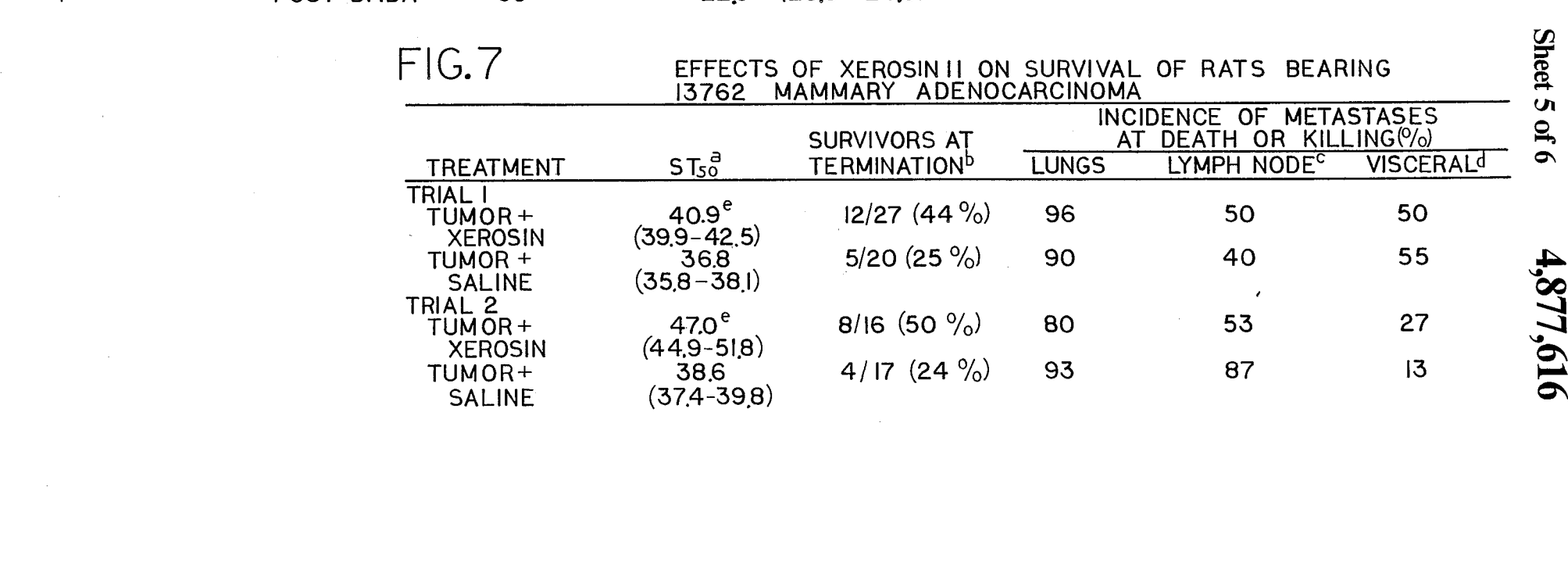
FIG. 7 is a table illustrating the effects of Xerosin II on the survival of rats bearing 13762 mammary adenacarcinoma.

As shown in FIG. 7, control rats bearing a single 1-mm$^3$ fragment of the 13762 mammary tumor had a median survival time of thirty-six (36) days after transplantation in two separate trials. The rats of the FIG. 7 table received 1-mm$^3$ implant of tumor three (3) days prior to initiation of Xerosin II treatment. In the table, (ST$_{50}$) indicates the survival time in number of days after implantation when 50% of the animals were alive. The numbers in parentheses reflect fiducial limits. For "survivors at Termination", the experiment terminated at fourty-two (42) (Trial 1) or fourty-seven (47) (Trial 2) days post implantation. The "Lymph Node" column refers to the axial lymph node on the side bearing the primary tumor while the "Visceral" column refers to the kidney and liver. The findings in the ST$_{50}$ column for the tumor and Xerosin trials were both significantly different from saline-treated control (p less than or equal to 0.05).

Figure 8A:
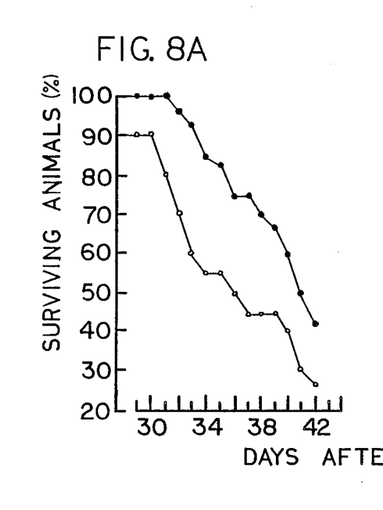
FIGS. 8A and 8B are graphs of the percent of surviving animals plotted against the days after implantation.
Figure 8B:
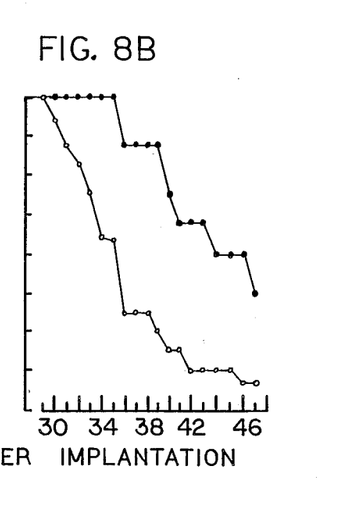

Most deaths occurred over a period of only a few days. The drop in the percentage of surviving animals, shown in FIGS. 8A and 8B, was precipitous. FIGS. 8A and 8B are graphs illustrating the effect of Xerosin II or saline injections three (3) times per week for four (4) weeks beginning three (3) days following implantation of 13762 mammary tumor fragment on survival. In Trial 1, FIG. 8A, a Xerosin II dose of 25 mg/kg per injection was used on seven (7) rats and is indicated by the filled circles. The open circles represent twenty (20) saline treated rats. In Trial 2, FIG. 8B, sixteen (16) rats were Xerosin treated and are noted by filled circles while seventeen (17) rats were saline treated and are noted by the open circles.

Also metastasis to the lungs occurred in greater than 90% of the control tumor-bearing rats, with involvement of tumor in regional lymph nodes and abdominal organs displaying more variability. Treatment with Xerosin II beginning three (3) days after tumor transplantation and continuing three (3) times per week for four (4) weeks improved survival time significantly in both trials, note FIGS. 8A and 8B again, amounting to a 12%–24% increase in survival. The average tumor diameters of the Xerosin and saline-treated groups were not significantly different. Note FIGS. 9A and 9B which are graphs of the effect of Xerosin II or saline injections on the growth of the 13762 mammary tumor as described in FIGS. 8A and 8B. The tumor size was calculated as the geometric mean of two (2) tumor diameters. The filled circles represent sixteen (16) Xerosin treated rats while the open circles represent seventeen (17) saline treated rats.

Figure 9A:
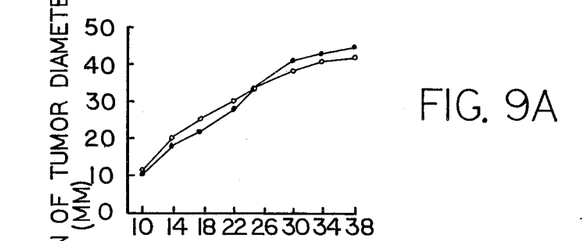
FIGS. 9A and 9B are graphs of the geometric mean of tumors, in millimeters, plotted against the days after implantation.
Figure 9B:
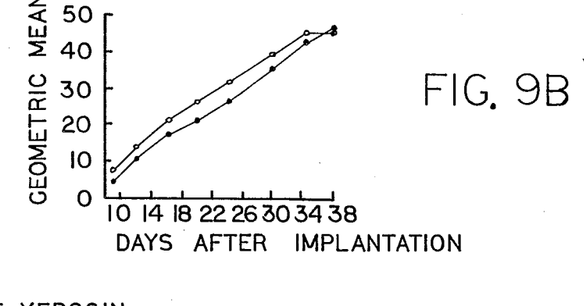

Furthermore, the incidence and pattern of distant metastases were not affected by the Xerosin II treatment of FIG. 9. Lung weights, taken as a measure of tumor burden, were also not reduced in the Xerosin-treated group.

These experiments have demonstrated that Xerosin II had biological activity in four different rodent bioassay systems. The protective effect of crude Xerosin against NDV-or endotoxin-induced mouse pneumonias, as described by Groupé et al, has been shown to be undiminished upon further purification yielding Xerosin II. In the chemically induced tumor system, injections of Xerosin II were most effective in reducing the number of tumor-bearing animals when treatment was begun prior to the appearance of the first palpable tumors following DMBA intubation. The effect of the Xerosin II treatment persisted for several weeks after the injections were stopped, but did not have a permanent effect, since the number of tumor-bearing animals in the Xerosin-treated group eventually reached that of the controls. For the carcinogenic action of DMBA to be permanently suppressed, long-term treatment with Xerosin II may be necessary.

It should be noted that even though Xerosin II treatment was effective in preventing the appearance of palpable mammary tumors for an extended period of time, it has no effect in reducing the actual number of tumors in a tumor-bearing rat. The Xerosin effect thus appears to be an all-or-nothing phenomenon, either completely successful in suppressing all tumors in an animal or completely ineffective in controlling multiple tumor foci.

The biologic activity of Xerosin II compares favorably with the effect of other potential immunostimulatory agents used to suppress mammary carcinogenesis induced by DMBA. Two laboratories have reported a reduction in mammary tumor incidence in the weeks following administration of DMBA. Kollmorgen et al used the methanol-extracted residue (MER) of Bacillus of Calmette and Guerin (BCG), while Nagasawa et al, treated rats with the cell wall skeleton (CWS) of Nocardia rubra (NR).

Xerosin II was not able to reduce growth of the 13762 tumor at the primary site. However, rats treated with Xerosin II during the four (4) week period following tumor transplantation had an improved time of survival. These data support the concept that Xerosin II is acting as a biological response modifier, improving the ability of the rat's own systems to fight off the tumor's challenge to survival.

Bartlett and Kreider have used the 13762 tumor line in ascites form for evaluating immune stimulants. They have reported no therapeutic effect in tumor growth rate or survival time after intravenous injection of Corynebacterium parvum. Survival times were improved and tumors regressed only when Corynebacterium parvum was administered intratumorally. The most successful treatment involved intratumoral injections of *Corynebacterium parvum* accompanied by subsequent surgical removal of the tumor at the site of implantation. BCG immunotherapy was less effective than *Corynebacterium parvum* treatment under comparable conditions. Thus, the systemic effects produced by subcutaneous injections of Xerosin II succeeded where intravenous treatment with *Corynebacterium parvum* failed in prolonging survival of tumor-bearing rats.

Figure 10:
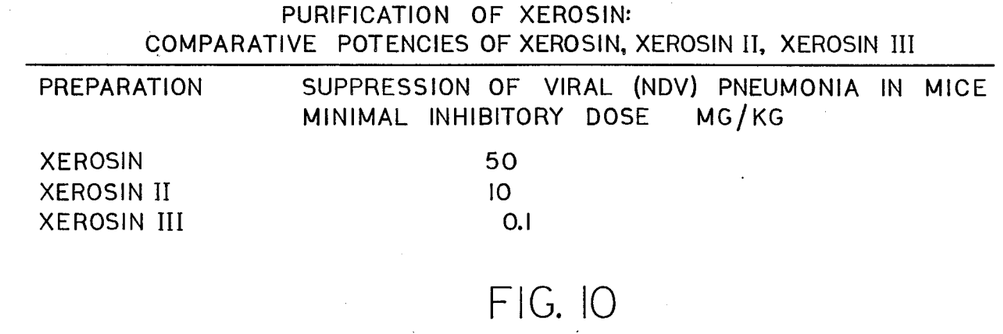
FIG. 10 is a table illustrating the comparative potencies of Xerosin APM, Xerosin II and Xerosin III.

As can be understood from the foregoing and from the information of the Table of FIG. 10, Xerosin II and Xerosin III may be considered as water-soluble complexes which are isolable from acid precipitable material recovered from cultures of the bacterium *Achromobacter xerosis* and which are effective in inducing a variety of biological responses and which exhibits significant therapeutic activity in higher vertebrates at a dosage ranging from about 0.1 to about 25.0 mg/kg of body. Xerosin II exhibits significant therapeutic activity in higher vertebrates at a dosage of as low as about 10.0 mg/kg of body weight or higher. Xerosin III exhibits significant therapeutic activity in higher vertebrates at a dosage as low as about 0.1 mg/kg of body weight or higher. Xerosin III has a molecular weight under approximately 100,000.

The method of inducing therapeutic biological responses in higher vertebrates thus comprises administering to a human or animal patient a therapeutically effective amount of a composition comprising a complex as defined above as an active agent. The composition is administered in an amount as shown in FIG. 10, sufficient to induce a therapeutic response in the patient. The therapeutic response is directed to treatment of diseases commonly affected by biological response modifiers.

Additionally, recent work carried out at Fort Detrick, Maryland under the direction of Dr. M. Chirigos demonstrated that Xerosin II provides radiation protection to mice and increases four (4) to twelve (12) fold the proliferation of human T-lymphocytes in the presence of suboptimal amounts of monoclonal antibody.

The above observations are of particular interest because one of the limiting factors to cancer treatment using X-radiation and standard cytotoxic drugs is damage to bone marrow leading to the absence of leucocytes, white blood cells, necessary for defense against infectious diseases.

The present disclosure includes that contained in the appended claims as well as that of the foregoing description. Although this invention has been described in its preferred forms with a certain degree of particularity, it is understood that the present disclosure of the preferred forms has been made only by way of example and that numerous changes in the details may be resorted to without departing from the spirit of the invention.

Now that the invention has been described, what is claimed is:

1. A method for preparing complexes by the purification of acid precipitated material (APM) recovered from cultures of the bacterium *Achromobacter xerosis* and which complexes are effective at a dosage of between about 10.0 to about 25.0 mg/kg of body weight in abating viral pneumonia in mice, the method of purification comprising the steps of:

growing a suitable culture of *Achromobacter xerosis* in a suitable growth medium using minimal agitation to achieve a relatively low oxygen tension;

recovering a water solubilized substance from acid precipitable material isolated from said culture in a conventional manner including a physical disruption of cells of said *Achromobacter xerosis*;

lyophilizing said water solubilized precipitate to dryness from a frozen state;

homogenizing said lyophilized product in distilled water at about pH 9;

heating the resultant solution readjusted to about pH 9 at about 80 degrees C. for about fifteen (15) minutes;

adjusting the solution to about pH 7;

removing insoluble material by centrifugation;

adding sodium sulfate to a final concentration of about 0.02M;

adding cetyltrimethylammonium bromide stock solution to about a 0.3% final concentration;

warming the resultant solution at about 37 degrees C. for about one (1) hour to form a precipitate;

clarifying the solution by centrifugation;

adding cold acetone to form a further precipitate;

collecting said precipitate by centrifugation; and washing said precipitate with acetone.

2. A method for preparing complexes by the purification of acid precipitated material (APM) recovered from cultures of the bacterium *Achromobacter xerosis* and which complexes are effective at a dosage of about 0.1 mg/kg of body weight in abating viral pneumonia in mice, the method of purification comprising the steps of:

growing a suitable culture of Achromobacter xerosis in a suitable growth medium using minimal agitation to achieve a relatively low oxygen tension;

recovering a water solubilized substance from acid-precipitable material isolated from said culture in a conventional manner including a physical disruption of cells of said Achromobacter xerosis;

lyophilizing said water solubilized precipitate to dryness from a frozen state;

homogenizing said lyophilized product in distilled water at about pH 9;

heating the resultant solution readjusted to about pH 9 at about 80 degrees C. for about fifteen (15) minutes;

adjusting the solution to about pH 7;

removing insoluble material by centrifugation;

adding sodium sulfate to a final concentration of about 0.02M;

adding cetyltrimethylammonium bromide stock solution to about a 0.3% final concentration;

warming the resultant solution at about 37 degrees C. for about one (1) hour to form a precipitate;

clarifying the solution by centrifugation;

adding cold acetone to form a further precipitate;

collecting said precipitate by centrifugation; and washing said precipitate with acetone;

purifying said precipitation by hydroxyapatite chromatography in a calcium phosphate column;

dissolving said purified precipitate by homegenation in water adjusted to about pH 9;

adjusting the resultant solution to about pH 7.5;

lyophilizing to dryness from a frozen state resulting in a composition which retains biological activity for long periods of time when stored in a closed container at room temperature; and filtering the composition in a Millipore filter.

* * * * *